United States Patent
Jiang et al.

(10) Patent No.: US 6,479,300 B1
(45) Date of Patent: Nov. 12, 2002

(54) METAL LOADED LIGAND BOUND MEMBRANES FOR METAL ION AFFINITY CHROMATOGRAPHY

(75) Inventors: Tongbo Jiang, Bedford, MA (US); Anthony J. DiLeo, Westford, MA (US); Ronald L. Bruening, American Fork, UT (US)

(73) Assignees: Millipore Corporation, Bedford, MA (US); IBC Advanced Technologies, Inc., American Fork, UT (US)

( * ) Notice: Subject to any disclaimer, the term of this patent is extended or adjusted under 35 U.S.C. 154(b) by 0 days.

(21) Appl. No.: 09/400,816

(22) Filed: Sep. 22, 1999

Related U.S. Application Data (63) Continuation-in-part of application No. 09/268,606, filed on Mar. 15, 1999.

(51) Int. Cl.[7] ............... G01N 33/53; G01N 33/543; B01J 20/00; C07K 1/00; B01D 11/00

(52) U.S. Cl. ............... 436/518; 436/86; 436/174; 436/177; 436/178; 436/518; 436/528; 436/529; 436/530; 436/531; 436/824; 502/401; 502/402; 502/405; 502/407; 502/415; 428/305.5; 428/422; 428/423.1; 428/432; 428/471; 428/475.5; 428/500; 428/516; 428/522; 428/523; 428/543; 530/344; 530/412; 530/413; 530/415; 530/416; 530/417; 530/418; 530/421; 530/426; 530/812; 210/198.2; 210/502.1; 210/634; 210/635; 210/638; 210/650; 210/651; 210/654; 210/660; 210/666; 210/670; 210/679; 210/681; 210/682; 210/684; 210/688

(58) Field of Search ............... 210/634, 638, 210/650, 660, 666, 681, 684, 198.2, 502.1, 635, 651, 654, 670, 679, 682, 688; 436/86, 174, 177, 178, 518, 528, 529, 530, 531, 824; 530/344, 412, 413, 415, 416, 417, 418, 421, 426, 812; 502/401, 402, 405, 407, 415; 428/305.5, 422, 423.1, 432, 471, 475.5, 500, 516, 522, 523, 543

(56) References Cited

U.S. PATENT DOCUMENTS

| 3,957,504 | A | * | 5/1976 | Ho et al. ............... 75/101 BE |
| 4,239,506 | A | * | 12/1980 | Steigelmann et al. ........ 55/16 |
| 4,360,434 | A | * | 11/1982 | Kawaguchi et al. ..... 210/500.2 |
| 4,541,952 | A | * | 9/1985 | Hosoi et al. ............ 260/112 R |
| 4,569,794 | A | | 2/1986 | Smith et al. ............... 260/113 |
| 4,618,533 | A | | 10/1986 | Steuck ....................... 428/315 |
| 4,877,830 | A | * | 10/1989 | Dobeli et al. ............. 525/54.3 |
| 4,902,481 | A | | 2/1990 | Clark et al. ................ 422/101 |
| 4,952,321 | A | * | 8/1990 | Bradshaw et al. ......... 210/670 |
| 5,015,268 | A | * | 5/1991 | Ho ............................... 55/16 |

(List continued on next page.)

FOREIGN PATENT DOCUMENTS

| EP | 0 253 303 A2 | 8/1987 |
| WO | WO 97/05159 | 2/1997 |
| WO | WO97/49492 | 12/1997 |

OTHER PUBLICATIONS

Beeskow et al. Nylon–based affinity membranes: impacts of surface modification on protein adsorption. J. Colloid Interface Sci. vol. 196, No. 2 (1997) pp. 278–291.*

(List continued on next page.)

*Primary Examiner*—Christopher L. Chin
*Assistant Examiner*—Kartic Padmanabhan
(74) *Attorney, Agent, or Firm*—Hamilton, Brook, Smith & Reynolds, P.C.

(57) ABSTRACT

Methods, compositions and devices for purifying polypeptides and/or proteins using metal loaded ligand bound membranes by metal ion affinity chromatography are described.

28 Claims, 3 Drawing Sheets

U.S. PATENT DOCUMENTS

| | | | | |
|---|---|---|---|---|
| 5,047,215 | A | | 9/1991 | Manns ........................ 422/101 |
| 5,078,978 | A | | 1/1992 | Tarbet et al. .................. 423/22 |
| 5,141,966 | A | | 8/1992 | Porath ......................... 521/32 |
| 5,169,936 | A | * | 12/1992 | Staples et al. ............... 530/350 |
| 5,182,251 | A | | 1/1993 | Bruening et al. ........... 502/401 |
| 5,250,188 | A | | 10/1993 | Bruening et al. ........... 210/672 |
| 5,273,660 | A | | 12/1993 | Bruening et al. ........... 210/670 |
| 5,284,933 | A | | 2/1994 | Döbeli et al. ................ 530/350 |
| 5,310,633 | A | | 5/1994 | Yoshida et al. ............. 430/458 |
| 5,326,533 | A | | 7/1994 | Lee et al. .................... 422/101 |
| 5,439,829 | A | * | 8/1995 | Anderson et al. ........... 436/518 |
| 5,547,760 | A | | 8/1996 | Tarbet et al. ................ 428/471 |
| 5,594,115 | A | | 1/1997 | Sharma ....................... 530/413 |
| 5,618,433 | A | | 4/1997 | Tarbet et al. ................ 210/634 |
| 5,698,104 | A | * | 12/1997 | Rhee et al. .................. 210/635 |
| 5,840,858 | A | * | 11/1998 | Smith et al. ................. 530/413 |
| 5,907,035 | A | * | 5/1999 | Guinn ......................... 530/412 |
| 6,045,821 | A | * | 4/2000 | Garrity et al. ............... 424/450 |
| 6,322,695 | B1 | * | 11/2001 | Lee et al. ................. 210/198.2 |
| 6,365,147 | B1 | * | 4/2002 | Luo et al. .................... 210/661 |

OTHER PUBLICATIONS

Kojima et al. Selective permeation of metal ions through cation exchange membrane carrying N–(8–quinolyl)sulfonamide as a chelating ligand. J. Membr. Sci. vol. 102, Nos. 1–2 (1995) pp. 49–54.*

Pack et al. A metal–chelating lipid for 2D protein crystallization via coordination of surface histidines. J. Amer. Chem. Soc. vol. 119, No. 10 (1997) pp. 2479–2487.*

Pack et al. Langmuir monolayer characterization of metal chelating lipids for protein targeting to membranes. Chem. and Phys. for Lipids. vol. 86, No. 2 (1997) pp. 135–152.*

Pabrosky, L.R. et al., "A Nickel Chelate Microtiter Plate Assay for Six Histidine–Containing Proteins," *Analytical Biochemistry* 234: 60–65 (1996).

Schmitt, J. et al., "Affinity Purification of Histidine–Tagged Proteins," *Mol. Biol.* 18: 223–230 (1993).

Micron®–SCX, "Adsorptive Microconcentrator for Peptides and DNA Oligomers".

Hochuli, E. et al., "New Metal Chelate Adsorbent Selective for Proteins and Peptides Containing Neighbouring Histidine Residues", *J. of Chrom.*, 411:177–184 (1987).

Kubota, N. et al., "Recovery of Serum Proteins Using Cellulosic Affinity Membrane Modified by the Immobilization of Cu2+ ion", *J. Applied Plymer Sci.*, 62(8):1153–1160 (1996).

Serafica, G.C. et al., "Protein Fractionation Using Fast Flow Immobilized Metal Chelate Affinity Resins", *Biotech. and Bioeng.*, 43:21–36 (1994).

Brandt, S. et al., "Membrane–Based Affinity Technology for Commerical Scale Purifications", *Biotechnology*, 6:779–782 (1988).

Smith, M.C. et al., "Immobilized Iminodiacetic Acid Metal Peptide Complexes. Indentification of Chelating Peptide Purification Handles for Recombinant Proteins", *Inorganic Chem.*, 26:1965–1969 (1987).

Yang, L. et al., "Immobilized Metal Affinity Composite Membrane Based on Cellulose for Separation of Biopolymers", *Chemical Abstracts*, vol. 130, No. 20, May 17, 1999.

* cited by examiner

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Synthetic

<400> SEQUENCE: 1

Gly Ser Ser His His His His His Ser Ser Gly Leu Val Pro Pro
1               5                   10                  15

Gly Ser
```

METAL LOADED LIGAND BOUND MEMBRANES FOR METAL ION AFFINITY CHROMATOGRAPHY

RELATED APPLICATION

This application is a continuation-in-part of U.S. Ser. No. 09/268,606 filed on Mar. 15, 1999, the entire teachings of which are incorporated herein.

BACKGROUND OF THE INVENTION

The rapid developments in recombinant DNA methodology have allowed the production of polypeptides, proteins, and their analogs in unlimited quantities in a very short period of time. These developments have created a need to handle purification of these proteins from complex mixtures in highly efficient and predictable manners.

Immobilized metal ion affinity chromatography (IMAC) has been used extensively to purify proteins containing exposed histidine and cysteine side chains. See Porath, J. et al., Nature, 258:598–599 (1975). Chelating agents selective for specific metal ions are coupled to a solid matrix, such as agarose beads or silica. For example, an active derivative of the chelating moiety nitrilotriacetic acid (NTA; N,N-bis[carboxymethyl]glycine) can be coupled to resins or solid matrices for use with metal ions having coordination numbers of six (e.g., $Ni^{2+}$), other chelating moieties include iminodiacetic acid (IDA) derivatives and tris(carboxymethyl) ethylenediamine. Sharma (U.S. Pat. No. 5,594,115) describes the use of $Ni^{2+}$ to purify histidine tagged peptides.

SUMMARY OF THE INVENTION

According to the method of the invention, polypeptides and/or proteins can be isolated and subsequently purified from an aqueous solution containing same by contacting the aqueous solution with a composition suitable for removing a peptide or protein of interest contained in said solution, then recovering the peptide or protein. Compositions useful for carrying out the methods of the invention comprise an ion-binding ligand bound to a membrane loaded with a metallic ion having an affinity for polypeptides/proteins contained in the aqueous solution. The membrane ligand combination is represented by the formula:

M-B-L-X wherein M is a membrane or composite membrane derivatized to have a hydrophilic surface and containing polar functional groups; L is a ligand having an affinity for metallic ions and containing a functional group reactive with an activated polar group from the membrane; B is a covalent linkage formed by the reaction between the activated polar group and the functional group of the ligand L; and X is a metallic ion chelated to L and has an affinity for polypeptides/proteins. The metallic ion is selected from the group consisting of cobalt (Co), nickel (Ni), copper (Cu), zinc (Zn) or combinations thereof.

Separation of peptides and/or proteins using membrane based metal ion affinity chromatography allows efficient and rapid removal of material, at high throughput, due to the high surface area provided by the membranes. Another advantage of membrane based separations is that equilibrium can be reached quickly. Further, micron-sized samples can be purified using an array of membranes, e.g., 96-well, 384-well and 1536-well separation devices, for automation purposes.

BRIEF DESCRIPTION OF THE DRAWINGS

The foregoing and other objects, features and advantages of the invention will be apparent from the following more particular description of embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention describes a method for purifying polypeptides and/or proteins using metal ion loaded ligand bound membranes, compositions comprising the metal loaded ligand bound membranes, and apparatus and devices (e.g., centrifugal devices) for separating polypeptides and/or proteins using the metal loaded ligand bound membranes described herein. The polypeptides and proteins can be efficiently isolated and purified by the present invention. As a result, high yields of isolated, biologically active proteins can be obtained. The present invention is directed at the purification of biologically active polypeptides and/or proteins (e.g., recombinant) from bacteria or non-bacterial sources, most preferably those recombinant proteins expressed in a soluble form or secreted from a host as a fusion protein containing a metal chelating or complexing peptide. In one embodiment of the invention, the protein of interest is produced as a fusion protein which, in addition to the amino acid sequence of the protein, contains a linker peptide. The linker peptide is a peptide capable of chelating a metal ion. When the peptide is contacted with the metal loaded ligand bound membrane of the present invention, the fusion protein containing the peptide is immobilized thereon. The desired polypeptide or protein, which is chelated or complexed to the membrane immobilized metal loaded ligand, may then be recovered by elution. In this embodiment, it is preferable that the ligand have a greater affinity for the metal ion than the peptides being removed from a solution to avoid removal of the metal from the ligand. It is noted that the polypeptide or protein must have an affinity for the metal ion X such that the polypeptide or protein can be removed from solution and recovered in purified form. The affinity can be in the form of a covalent or ionic bond.

Thus, this invention involves a process for separating biologically active polypeptides and/or proteins from impurities. By the term "biologically active polypeptides and proteins" is meant polypeptides and proteins that are themselves biologically active or polypeptides and proteins that are useful in the production of biologically active polypeptides and proteins. The polypeptides and proteins referred to herein can be naturally occurring or synthetic, and, if synthetic, can be produced by classical solution phase, by solid phase, or by recombinant DNA methodology.

Preferably, the polypeptides and proteins contemplated herein are those produced via recombinant DNA methodology. The polypeptides and proteins of interest further comprise one or more peptides capable of chelating or complexing with a metal bonded to a ligand of an immobilized ligand bound membrane. As such, at least one peptide must be capable of complexing or chelating with the divalent metal ions of metals selected from the group consisting of cobalt, nickel, copper, zinc and combinations thereof.

Two important characteristics of the ligand bound membrane are (1) that it is capable of chelating or complexing an immobilized metal ion and (2) that the chelating ability of the metal ion is maintained such that the chelated metal additionally attaches to a biologically active polypeptide or protein. Many peptides will chelate metal ions under conditions in which both the ion and the peptide are free from external constraints. However, when the metal ion has been immobilized on the ligand, the availability of the metal for chelation is more restricted. Moreover, when the peptide which exhibits chelating activity is also joined to or forms as a part of another entity, i.e., a biologically active polypeptide or protein, the potential for chelation may be reduced. Suitable preferred peptides capable of binding to metal ligands are those having at least one amino acid selected from the group consisting of histidine and cysteine. Presumably, the thiol group on the cysteine and the imidizol group on the histidine are the coordination or complex sites with which the metal loaded ligand immobilization on a membrane attaches. This is possible because the metal does not use all of its coordination sites when binding to the ligand, leaving sites available for the peptide and/or protein to bind. Most preferred peptides are those containing histidine. See U.S. Pat. Nos. 4,569,794, 5,284,933, 5,310,663 and 5,326,533. The entire teachings of these references are incorporated herein by reference.

The general method for removing peptides and/or proteins of interest from aqueous solutions comprises contacting the aqueous solution with a composition suitable for capturing (e.g., by chelation or by forming a complex) peptides and/or proteins contained in said solution, then recovering the isolated protein and/or peptides. Compositions useful for carrying out the methods of this invention comprise an ion-binding ligand membrane loaded with a metallic ion having an affinity for peptides or proteins containing histidine and/or cysteine (e.g., histidine and cysteine side chains on the proteins and/or peptides of interest contained in solution). The membrane ligand loaded with a metallic ion is represented by the formula:

$$M\text{-}B\text{-}L\text{-}X$$

wherein M is a membrane or composite membrane derivatized to have a hydrophilic surface and containing polar functional groups; L is a ligand having an affinity for metallic ions (e.g., cobalt, nickel, copper, zinc and combinations thereof) and containing a functional group reactive with an activated polar group from the membrane; B is the covalent linkage formed by the reaction between the activated polar group and the functional group of the ligand; and X is a metallic ion (e.g., selected from the group consisting of cobalt, nickel, copper, zinc and combinations thereof) chelated to L and has an affinity for the polypeptide/protein.

Representative of B linkages are members selected from the group consisting of amide (NHCO), ester (COO), thioester (COS), carbonyl (CO), ether (O), thioether (S), sulfonate ($SO_3$) and sulfonamide ($SO_2NH$). X is a metallic ion chelated to L and has an affinity for the polypeptides/proteins.

The metal loaded ligand affixed the membrane functions to attract the desired polypeptide and/or protein according to the following formula:

$$M\text{-}B\text{-}L\text{-}X+P \rightarrow M\text{-}B\text{-}L\text{-}X\text{-}P$$

wherein M-B-L-X represents the metal loaded ligand affixed to a membrane as described previously and P represents the desired polypeptide and/or protein. Further, the polypeptide and/or protein may be recovered according to the following formula:

$$M\text{-}B\text{-}L\text{-}X\text{-}P+E \rightarrow M\text{-}B\text{-}L\text{-}X+P$$

wherein E represents an elution method used to recover the polypeptide/protein complexed to the metal loaded ligand bound membrane.

The filtration/purification process of the invention can be carried out in any manner that provides for bringing the aqueous solution containing peptides and/or proteins of interest into contact with the metal loaded ligands affixed to the membrane. The preferred embodiment disclosed herein involves carrying out the process by bringing the aqueous solution into contact with a composition of matter of the invention. Contact is preferably made in a contacting device comprising a housing (e.g., a cartridge) containing the composition of matter of the invention and causing the aqueous solution to flow through the housing (e.g., the cartridge) and thus come in contact with the composition of the invention. The contacting device can include means for flowing a source solution and a receiving solution past said ligand-membrane composition. Alternatively, the membrane configuration is in the form of a multi-well plate, such as a 96, 384 or 1536 well plate, although other membrane configurations, such as flat sheet, stacked disk, hollow fibers or pleated membrane may be used. However, various contact apparatus may be used instead of cartridges.

The ligand bound membrane, loaded with a metal ion, can be used batch-wise in continuously operating columns to purify the polypeptides and proteins. Prior to loading with the sample, the ligand bound membrane loaded with a metal ion is equilibrated with an aqueous buffer, such as a phosphate buffer at pH 8. The equilibration buffer (and the elution buffer) can contain a denaturing agent or a detergent such as guanidine-HCl, urea or TRITON® (octyphenyl oxide condensate). The addition of such a denaturing agent or detergent permits problem-free operations even with polypeptides and proteins which are poorly soluble in aqueous solution.

An important portion of the process of this invention involves recovering (e.g., by elution) the biologically active polypeptide or protein from the metal loaded ligand bound membrane following its selective adsorption. Generally, either of two recognized elution methods can be employed. The pH of the buffer may be lowered or a displacing ligand may be added to the buffer. In the former, the lowered pH protonates the coordinating groups, e.g., the imidazole ring of the histidine, on the polypeptide or protein, making the coordinating group incapable of forming a coordination complex with the immobilized metal ions. This allows for the polypeptides and proteins to be washed from the membrane using a low pH buffer.

In the latter elution method, by adding a displacing ligand to the buffer, dissociation of the polypeptides and proteins from immobilized metal ions occurs. This method is especially useful if the polypeptide or protein of interest cannot tolerate a low pH environment. The displacing ligand competes with the polypeptide or protein at coordination sites of the metal ion if its affinity for the latter is greater than that of the bound polypeptide or protein. An example of such a displacing ligand is ethylene-diaminetetraacetic acid (EDTA). Certain ligands can achieve displacement even if their binding affinity is not substantially greater than that of the bound polypeptide or protein if they are present in a large excess relative to the bound polypeptide or protein. Examples of such ligands are glycine, histidine, ammonia and the like. The optimal elution conditions depend on the amount and type of impurities which are present, the amount of material to be purified, the column dimensions, etc., and are easily determined by routine experimentation on a case-by-case basis.

The membrane may then be regenerated by stripping the metal ion using a strong acid (e.g., 6M HCl) to protonate the ligand thereby disassociating the metal ions. The membrane can then be stripped using a strong acid by methods known in the art and subsequently reloaded by methods as described in the present invention (see Example 1 for one embodiment regarding reloading).

Compositions useful in the present invention comprise metal ion bound ligands that are covalently bonded to a membrane through an amide, ester, thioester, carbonyl or other suitable bond and have been described in detail in U.S. Pat. No. 5,618,433 and U.S. Ser. No. 08/745,026; the entire teachings of which are incorporated herein by reference. Membranes that are inherently hydrophilic, or partially hydrophilic, and contain moieties appropriate for making these bonds are preferred. Such membranes include polyamides, such as nylon, and cellulosic materials, such as cellulose, regenerated cellulose, cellulose acetate, and nitrocellulose. If the membrane used does not contain reactive groups it may be modified or derivatized appropriately.

Composite membranes are also useful. A composite membrane comprises a porous polymer membrane substrate and an insoluble, cross-linked coating deposited thereon. The porous polymer is selected from the group consisting of fluorinated polymers, polyolefins, polystyrenes, polysulfones, polyesters, polyacrylates, polycarbonates, vinyl polymers and polyacrylonitriles. For example, representative suitable polymers forming the membrane substrate include fluorinated polymers including poly(tetrafluoroethylene) ("TEFLON"), polyvinylidene fluoride (PVDF), and the like; polyolefins such as polyethylene, ultra-high molecular weight polyethylene (UPE), polypropylene, polymethylpentene, and the like; polystyrene or substituted polystyrenes; polysulfones such as polysulfone, polyethersulfone, and the like; polyesters including polyethylene terephthalate, polybutylene terephthalate, and the like; polyacrylates and polycarbonates; polyethers including perfluorinated polyethers; and vinyl polymers such as polyvinyl chloride and polyacrylonitriles. Copolymers can also be used for forming the polymer membrane substrate, such as copolymers of butadiene and styrene, fluorinated ethylene-propylene copolymer, ethylene-chlorotrifluoroethylene copolymer, and the like. The preferred membrane is composite membrane comprising ultrahigh molecular weight polyethylene having a hydrophilic coating containing carboxylic groups, such as those described in U.S. Pat. Nos. 4,618,533 and 5,618,433.

With composite membranes, the substrate membrane material is not thought to affect that performance of the derivatized membrane and it is limited in composition only by its ability to be coated, or have deposited on its surface, an insoluble polymer layer that contains the appropriate reactive group. This provides a hydrophilic layer which interacts well with water or other aqueous solutions with no appreciable change in pore size or flow characteristics. The end result is that when the ligand is attached to the surface of either a hydrophilic membrane or a composite membrane having a hydrophilic surface, the basic characteristics of any given ligand molecule are not changed by the process of attaching it to the surface or by the nature of the surface itself.

The coating of the composite membrane comprises a polymerized cross-linked monomer such as acrylates, methacrylates, ethacrylates, acrylic acid, acrylamides, methacrylamides, ethacrylamides and mixtures thereof. Representative suitable polymerizable monomers include hydroxyalkyl acrylates or methacrylates including 1-hydroxyprop-2-yl acrylate and 2-hydroxyprop-1-yl acrylate, hydroxypropylmethacrylate, 2,3-dihydroxypropyl acrylate, hydroxyethylacrylate, hydroxyethyl methacrylate, and the like, and mixtures thereof. Other polymerizable monomers that can be utilized include acrylic acid, 2-N,N-dimethylaminoethyl methacrylate, sulfoethylnethacrylate and the like, acrylamides, methacrylamides, ethacrylamides, and the like. Other types of hydrophilic coatings that can be used within the scope of the invention include expoy functional groups such as glycidyl acrylate and methacrylate, primary amines such as aminoethyl methacrylates, and benzyl derivatives such as vinyl benzyl chloride, vinyl benzyl amine, and p-hydroxyvinyl benzene.

The basic consideration in selecting a composite membrane is that the coating placed on the membrane substrate is the determining factor in defining the chemistry used to covalently attach the ligand. For example, a composite membrane displaying a carboxylic acid functional group can form an amide bond with a pendant amine group from the ligand, one of the most stable methods of ligand immobilization. The composite polymers referenced above can be prepared with carboxylic acid active groups that can be readily converted to amides upon reaction with an amine group on a ligand. However, any of the other organic species which are reactive toward an acid chloride could be used to attach an organic ligand to the surface. Additional examples of such groups would be esters, thioesters, Grignard reagents, and the like. If the reactive group on the surface is a sulfonic acid, then an analogous procedure using a sulfonyl chloride would yield results similar to those obtained with carboxylic acid functionalities. One such polymer containing sulfonic acid reactive groups is available under the tradename NAFION® from DuPont as described above. Preferably, suitable ligands contain an ester or carboxyl group and an amine to form an amide linkage.

The composite membrane comprises a membrane substrate formed of a first polymer and having coated thereon a second polymer having a hydrophilic surface. The second polymer can be coated onto the first polymer by a precipitated crystal technique. Alternatively, the surface of the first polymer is coated with a cross-linked second polymer formed from a monomer polymerized in situ and cross-linked in situ on the substrate. In one embodiment, the coating of composite membranes also comprises a precipitated crystal system, such as that involving the material known under the trademark NAFION®. NAFION® is a sulfonic acid or sodium sulfonate of a perfluorinated polyether. In another embodiment, the preferred coating is commercially available as RINSEGUARD® (Millipore Corporation); U.S. Pat. No. 4,618,433.

The class of ligands (L) that are suitable for binding metal ions (X) that, in turn, can further bind to polypeptides and proteins, are those that, when covalently bound through linkage B to the membrane and complexed to the metal X, have no net electrical charge. In other words the ligand is neutral. Exemplary of suitable ligands are pyridine containing ligands, such as those containing 2-pyridyl or 2-substituted pyridyl groups, and N-cyclic aromatic hydrocarbon-containing ligands preferably containing at least four N-cyclic groups of which pyridine, pyrimidine, pyrazine, imidazole, quinoline, isoquinoline, naphthyridine, pyridopyridine, phananthroline are representative. Such ligands are described in U.S. Pat. Nos. 5,078,978, 5,182,251, 5,273,660, 5,547,760, 5,250,188 and PCT Publication WO 97/49492. A particularly preferred ligand is SUPERLIG 422® (pyridine containing ligand) from IBC Corp. These ligands are only meant to be representative and any other ligands that are functional for the purposes states herein may be used and are considered to be within the scope of this invention.

The compositions of the present invention may be prepared by any suitable method wherein the ligands can be covalently bonded to a membrane containing reactive functional groups. See U.S. Pat. No. 5,618,433, issued Apr. 8, 1997, the entire teachings of which are incorporated herein by reference. For example, immobilization of the ligand onto the membrane is carried out in a two step procedure: [1] activation and [2] coupling. The activation procedure involves reaction of carboxylic acid groups on membranes with 1-Ethyl-3-(3-Dimethylaminopropyl) carbodiimide Hydrochloride (EDAC) in either water or IPA/water medium to produce a reactive intermediate compound. In the coupling step this reactive intermediate compound reacts with the amine group on the linker arm attached to the ligand, producing the ligand immobilized membrane surface. The immobilization procedure can be carried out for multiple ligands that are immobilized one at a time (in series), or for multiple ligands co-immobilized simultaneously. In a preferred embodiment, the membrane is an ultrahigh molecular weight polyethylene having a hydrophilic coating, the ligand is covalently attached thereto via amide bonds. The hydrophilic coating is an ultra-high-density polyurethane available under the trademark, RINSEGUARD™ (Millipore Corp., U.S. Pat. No. 4,618,433).

The membrane/ligand compositions that are useful for carrying out the present invention will be apparent to those skilled in the art by the following examples each of which utilizes a composite membrane prepared according to U.S. Pat. No. 4,618,433 and containing carboxylic acid groups or sulfonic acid groups. The membranes should have a microporous or ultraporous structure. The ligands may be attached to the upstream outer surface of the membrane, the downstream outer surface of the membrane, the inner porous surface of the membrane or any combination of these surfaces. Preferably, the entire surface of the membrane, including the pores, contain ligands.

The invention also pertains to an apparatus suitable for separating polypeptides and/or proteins from liquid samples. The apparatus comprises a plate having a plurality of wells, each of the wells having a first open end, a second end and an outside peripheral surface. Each well contains a metal loaded ligand bound membrane in sealing relationship with each of the second ends. The apparatus further comprises a template having a plurality of holes of a size and arrangement corresponding to said wells, said template being positioned so as to retain said membrane in sealing relationship with the second end and outside peripheral surface of each of said wells, and each second end extending through said template. The apparatus can include a container for a liquid composition in direct contact with said membrane sealed to the second end of said at least one well. The inner peripheral surface of the second end can include a shelf.

In one embodiment, this invention provides an improved multiwell apparatus which permits separating a plurality of samples simultaneously while avoiding contamination among samples. The metal loaded ligand bound membrane, described herein, is sealed to open ends of a multiwell apparatus by means of a template which secures the membrane tightly to one end of each well. The membrane on each well is positioned relative to the template so that the formation of air pockets at the membrane surface is avoided during sample separations.

Figure 1:
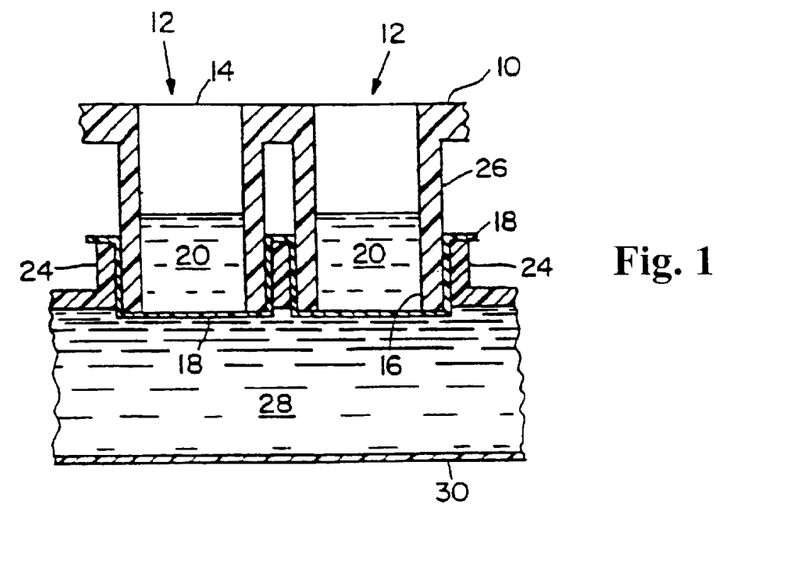
FIG. 1 is a cross-sectional view of the apparatus of this invention.
Figures 2, 4:
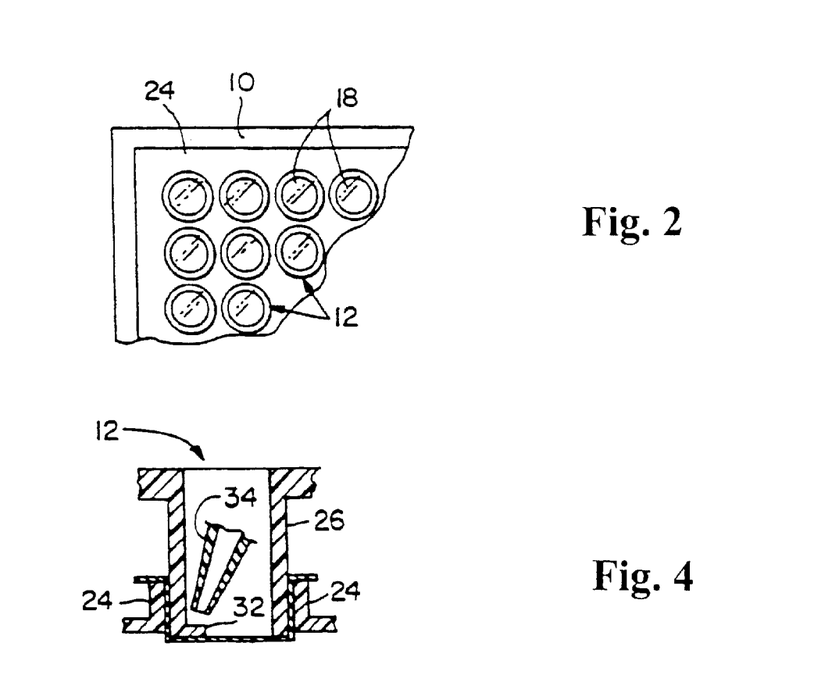
FIG. 2 is a bottom view of the apparatus of this invention.
FIG. 4 is a cross-sectional view of an apparatus of this invention which includes a shelf in the well.
Figure 3:
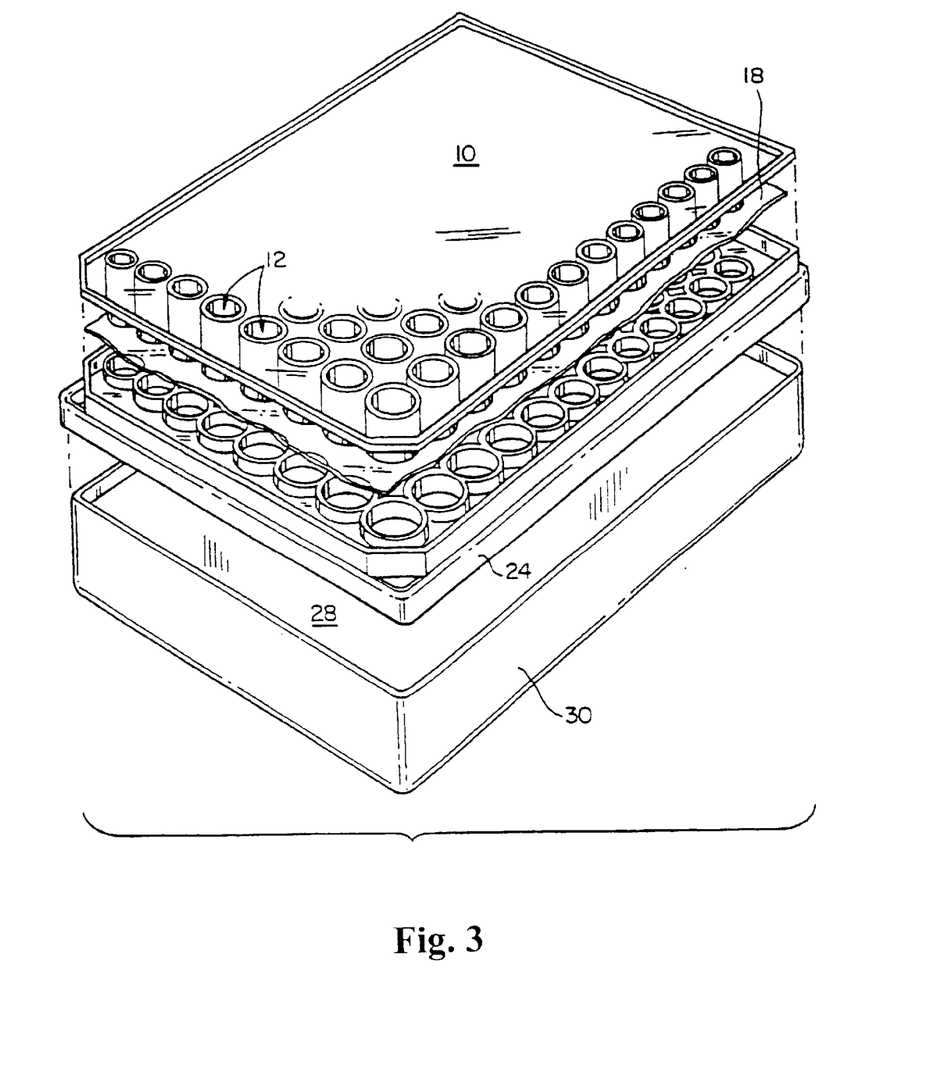
FIG. 3 is an exploded view of the apparatus of this invention.

Referring to FIGS. 1 through 3, plate 10 includes a plurality of wells 12. Each well 12 has an open end 14 and a second end 16 which is sealed by the metal loaded membrane/ligand composition 18, as described herein. Sample 20 is retained within well 12. Membrane 18 is retained in sealing relationship with end 16 by means of template 24. Template 24 has a plurality of holes of a size and position so that they mate with the extension surface 26 of wells 12 adjacent end 16 with the membrane 18 frictionally held between the well surface 26 and the template. The portion of the membrane 18 which contacts end 16 is spaced apart from template 24 so that it extends into a solution 28 such as a dialysate within container 30 so that air bubbles are avoided between the membrane 18 and solution 28.

The membrane 18 can be sealed to the bottom of the wells 12 either as a continuous sheet (see U.S. Pat. No. 5,047,215) or as individual filters over the end of each well 12 (see U.S. Pat. No. 4,902,481).

Referring to FIG. 4, the wells 12 of this invention can include a shelf 32 at the end thereof in contact with the metal loaded membrane/ligand composition 18. The shelf 32 is useful to position a pipette 34 for introducing or removing liquid into or from the well 26 while avoiding contact of the membrane 18 with the pipette 34. The shelf 32 materially reduces the possibility of rupturing membrane 18 with pipette 34.

In another embodiment of this invention, the membranes described herein can be used in filtration devices that can be centrifuged. The membrane can be sealed or attached to the device. The peptide or protein of interest can be isolated from the solution as it passes through the filter. The isolated peptide or protein can then be recovered by elution using known techniques. A particularly preferred centrifugal filtration device is commercially available from Millipore under the trademark MICROCON®-SCX, (strong-cation-exchange-membrane microconcentrator) which is compatible with microcentrifuges.

The following examples illustrate the present invention and are not intended to be limiting in any way. All references cited herein are incorporated by reference in their entirety.

EXAMPLES

Example 1

Ni Ion Capacity Obtained at Different Amounts of Loading

A ligand bound membrane was soaked overnight in a 50 mM acetate buffer at pH 3.5 spiked with different amounts of $NiCl_2$ (ligand=SL 422; IBC Advanced Technologies, Inc., American Fork, Utah; membrane=hydrophilic ultra high molecular weight polyethylene). The Ni ion capacity on membrane was analyzed by Inductively Coupled Plasma-Mass Spectroscopy (ICPMS) after being stripped off in 6M HCl. The loading efficiency ranged from 88–98% and the maximum capacity was 1.22 $\mu mol/cm^2$, as shown in Table 1.

TABLE 1

| Amount of Ni ion in loading solution ($\mu$mol/cm$^2$) | Ni ion capacity on membrane ($\mu$mol/cm$^2$) | Loading efficiency |
|---|---|---|
| 3.06 | 1.22 | / |
| 1.84 | 1.22 | / |
| 0.92 | 0.84 | 92% |
| 0.61 | 0.56 | 92% |
| 0.31 | 0.29 | 95% |
| 0.10 | 0.09 | 88% |
| 0.03 | 0.03 | 98% |

Example 2

Equilibrium Capacity of the Ni Loaded Membrane for a Peptide Containing 6 Histidine The peptide sequence was GSSHHHHHSSGLVPPGS (SEQ ID No.:1). Two and half $\mu$mol of the peptide was prepared in a 100 mM phosphate buffer of pH 8.0. The peptide solution was recirculated through a 13-mm membrane (hydrophilic ultra high molecular weight polyethylene), which was previously loaded with Ni ion at full capacity (SL 422; IBC; U.S. Pat. No. 5,078,978). The flow rate was set at 0.5 ml/min. At the end of 2 hours, the filtrate was taken out and the same buffer was applied to wash continuously until the peptide concentration became nondetected. The bound peptide was then eluted by a 100 mM phosphate buffer of pH 5. The peptide concentration was measured by UV absorption at 214 nm. The equilibrium capacity for the peptide was 0.134 $\mu$mol/cm$^2$.

TABLE 2

| | |
|---|---|
| Peptide in feed | 2.5 $\mu$mol |
| Peptide in filtrate | 2 $\mu$mol |
| Peptide in wash | 0.315 $\mu$mol |
| Peptide in eluant | 0.094 $\mu$mol |
| Recovery | 96% |
| Peptide capacity | 0.134 $\mu$mol/cm$^2$ |

Example 3

The Stoichiometry of the Reaction

The above experiment was repeated on the Ni loaded membrane with different pore size. Relationship between the ion exchange capacity (IEC) of the base membrane, the Ni capacity and the equilibrium capacity of the peptide was studied. The data listed in Table 3 revealed that the equilibrium capacity of the peptide was proportional to the Ni capacity, which was then directly related to the ion exchange capacity (IEC) of the base membrane. The ratio of the peptide capacity to the Ni capacity ranged from 1:10 to 1:20, mostly due to the stereo hindrance and the diffusion limitation.

TABLE 3

| Sample ID | Thickness ($\mu$) | IEC ($\mu$mol/cm2) | Ni capacity ($\mu$mol/cm2) | Peptide Capacity ($\mu$mol/cm2) | Ratio (Peptide/Ni) |
|---|---|---|---|---|---|
| 0.15$\mu$, thin | 43 | 1.7 | 0.64 | 0.061 | 1:10 |
| 0.25$\mu$, thin | 47 | NA | 0.45 | 0.036 | 1:12 |
| 0.45$\mu$, thick | 142 | NA | 0.74 | 0.036 | 1:20 |
| 0.65$\mu$, thick | 128 | 3.5 | 1.34 | 0.134 | 1:10 |

Example 4

Breakthrough Curve of the Ni Loaded Membrane at Different Flow Rate

Figure 5:
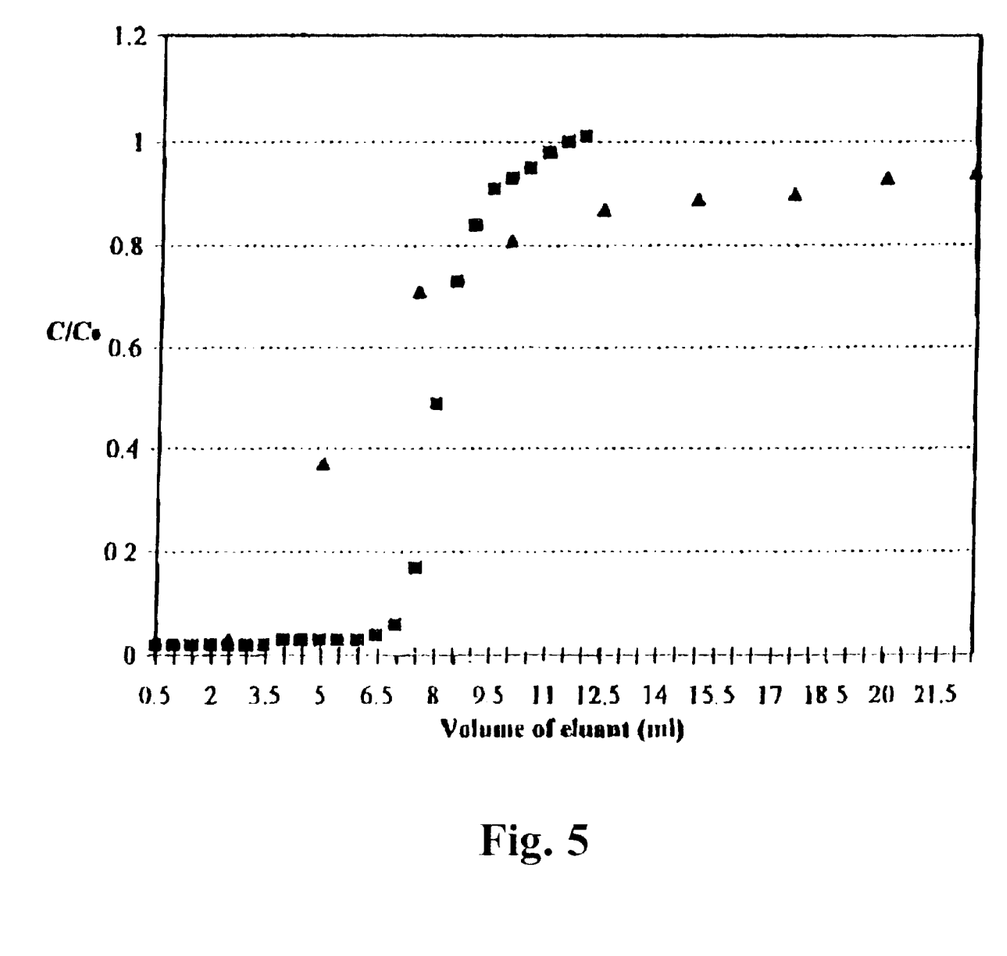
FIG. 5 is a break through curve of Ni loaded membrane at flow rates of 0.25 ml/min (squares) and 2.5 ml/min (triangles).

The peptide solution prepared at 100 $\mu$M was flown through a 25 mm Ni loaded membrane at two different flow rates: 0.25 ml/min and 2.5 ml/min. The peptide concentration in the filtrate was monitored continuously until it became constant. FIG. 5 shows a breakthrough curve obtained at those flow rates. At 0.25 ml/min, the breakthrough occurred at a larger volume; in addition, the reaction kinetics was much more improved.

Example 5

Dynamic Capacity for the 6-His Peptide on a MULTISCREEN® Plate (Millipore)

The Ni loaded membrane (SL 422; IBC; hydrophilic ultra high molecular weight polyethylene) was bound to a MULTISCREEN® 96-Well Assay Plate (MS; Millipore) by a heat sealing process. An experiment was done to confirm that the Ni loading remained the same after being immersed in the buffer for overnight. The dynamic capacity was measured on the MS plate by filtering 200 $\mu$l peptide solution prepared at different concentration, washing and eluting at 1 minute flow time. The peptide concentration in the eluant was detected by UV214. Each sample had at least duplicates. Due to the detection limit of the instrument, peptide concentrations at 1 $\mu$M were not detected.

TABLE 4

| Peptide Concentration | 100 $\mu$M | 10 $\mu$M | 1 $\mu$M |
|---|---|---|---|
| Dynamic capacity (nmol/well) | 20 | 0.4 | Not detected |
| Recovery (%) | 100% | 21% | Not detected |

The dynamic capacity achieved was tremendous compared to the traditional 96-well plate, which was in the range of pmol/well. This significant improvement was resulted from the combined use of the membrane and the ligand. The above data also suggested that the reaction be kinetically controlled at this flow rate, as the recovery dropped significantly with decreasing concentration. In order to improve recovery at low concentrations, residence time must be increased to allow enough time for the peptide to react with the immobilized Ni ion.

Example 6

Feasibility of Using Cu Ion for the Peptide Binding

The membrane (hydrophilic ultra high molecular weight polyethylene) immobilized with the same ligand (SL 422; IBC) was loaded with Cu ion at full capacity and tested for the peptide binding. The following results (Table 5) showed that the immobilized Cu ion bound the peptide in a similar way as Ni ion. Similar results are expected with Co and Zn ions, as well.

TABLE 5

| Sample ID | Metal Ion capacity (μmol/cm²) | Peptide capacity (μmol/cm²) | Ratio (Peptide/Metal ion) |
|---|---|---|---|
| Ni | 1.34 | .134 | 1:10 |
| Cu | 0.77 | .051 | 1:15 |

Since selectivity can be varied by choice of type of ligand and metal ion, this invention can offer a great degree of flexibility in choosing the metal ion for the immobilization for the best results.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for separating a polypeptide or protein from an aqueous solution, comprising contacting said solution with a ligand bound membrane loaded with a metal ion and recovering the polypeptide or protein from the membrane; wherein the metal ion loaded ligand bound membrane is represented by the formula:

M-B-L-X wherein M is a membrane or composite membrane derivatized to have a hydrophilic surface and contain polar functional groups; L is a ligand having an affinity for X and containing a functional group reactive with an activated polar group from the membrane and selected from the group consisting of N-cyclic amine-containing hydrocarbons, pyridine containing hydrocarbons and combinations thereof; B is a covalent linkage formed by the reaction between the activated polar group and the functional group of the ligand; and X is a metallic ion chelated to L and has an affinity for the polypeptide/protein via available coordination site(s) on X; wherein X remains bound to L under conditions for removal of the polypeptide or protein from X.

2. The method according to claim 1 wherein B is a covalent linkage selected from the group consisting of amide (NHCO), ester (COO), thioester (COS), carbonyl (CO), ether (O), thioether (S), sulfonate ($SO_3$) and sulfonamide ($SO_2NH$) linkages.

3. The method according to claim 2 wherein M is a polyamide membrane.

4. The method according to claim 3 wherein said membrane is a polyamide comprising nylon.

5. The method according to claim 2 wherein M is a composite membrane comprising a membrane substrate formed of a first polymer, said substrate being directly coated on its entire surface with a second polymer by a precipitated crystal technique and having a hydrophilic surface.

6. The method according to claim 5 wherein said first polymer is a polymer or copolymer of a member selected from the group consisting of fluorinated polymers, polyolefins, polystyrenes, polysulfones, polyesters, polyacrylates, polycarbonates, vinyl polymers and polyacrylonitriles.

7. The method according to claim 6 wherein said second polymer is a perfluorinated polyether.

8. The method according to claim 2 wherein M is a composite membrane comprising a membrane substrate formed of a first polymer, said substrate being directly coated on its entire surface with a cross-linked second polymer formed from a monomer polymerized in situ and cross-linked in situ on said substrate and having a hydrophilic surface.

9. The method according to claim 8 wherein said first polymer is a polymer or copolymer of a member selected from the group consisting of fluorinated polymers, polyolefins, polystyrenes, polysulfones, polyesters, polyacrylates, polycarbonates, vinyl polymers and polyacrylonitriles.

10. The method according to claim 9 wherein said second polymer is formed from a polymerizable monomer selected from the group consisting of acrylates, methacrylates, ethacrylates, acrylic acid, acrylamides, methacrylamides, ethacrylamides and mixtures thereof.

11. The method according to claim 10 wherein L is a poly-N-cyclic amine containing hydrocarbon ligand.

12. The method according to claim 10 wherein L is a pyridine-containing hydrocarbon ligand.

13. The method according to claim 2 wherein B is an amide linkage.

14. The method according to claim 2 wherein B is a sulfonamide linkage.

15. The method according to claim 1 wherein X is selected from the group consisting of nickel, copper, cobalt, zinc and combinations thereof.

16. The method according to claim 1 wherein the metal ion loaded ligand bound membrane is contained in a contacting device for holding said composition, wherein said contacting device includes means for flowing a source solution and receiving solution past said composition.

17. The method according to claim 16 wherein said contacting device is a cartridge.

18. The method of claim 1 wherein the polypeptide or protein comprises a histidine and/or cysteine.

19. A method for separating a polypeptide or protein from an aqueous solution, comprising contacting said solution with a metal ion loaded ligand bound membrane represented by the formula:

M-B-L-X wherein M is a membrane or composite membrane derivatized to have a hydrophilic surface and contain polar functional groups; L is a ligand having an affinity for X and containing a functional group reactive with an activated polar group from the membrane and selected from the group consisting of N-cyclic amine-containing hydrocarbons, pyridine containing hydrocarbons and combinations thereof; B is a covalent linkage formed by the reaction between the activated polar group and the functional group of the ligand; and X is a metallic ion chelated to L and has an affinity for the polypeptide/protein via available coordination site(s) on X; wherein X remains bound to L under conditions for removal of the polypeptide or protein from X.

20. The method according to claim 19 wherein M is a polyamide membrane.

21. The method according to claim 19 wherein L is a poly-N-cyclic amine containing hydrocarbon ligand.

22. The method according to claim 19 wherein L is a pyridine-containing hydrocarbon ligand.

23. The method according to claim 19 wherein X is selected from the group consisting of nickel, copper, cobalt, zinc and combinations thereof.

24. The method according to claim 19 wherein the metal ion loaded ligand bound membrane is contained in a contacting device for holding said composition, wherein said contacting device includes means for flowing a source solution and a receiving solution past said composition.

25. The method according to claim 24 wherein said contacting device is a cartridge.

26. A method for separating a polypeptide or protein from an aqueous solution, comprising contacting said solution with a ligand bound membrane loaded with a metal ion and recovering the polypeptide or protein from the membrane; wherein the metal ion loaded ligand bound membrane is represented by the formula:

M-B-L-X wherein M is a composite membrane comprising a porous substrate coated with a cross-linked hydrophilic polymer having polar functional groups; L is a ligand having an affinity for X and containing a functional group reactive with an activated polar group from the membrane and selected from the group consisting of N-cyclic amine-containing hydrocarbons, pyridine containing hydrocarbons and combinations thereof; B is a covalent linkage formed by the reaction between the activated polar group and the functional group of the ligand; and X is a metallic ion chelated to L and has an affinity for the polypeptide/protein via available coordination site(s) on X; wherein X remains bound to L under conditions for removal of the polypeptide or protein from X.

27. The method of claim 26, wherein the porous substrate is a polymer or copolymer selected from the group consisting of fluorinated polymers, polyolefins, polystyrenes, polysulfones, polyesters, polyacrylates, polycarbonates, vinyl polymers and polyacrylonitriles.

28. The method of claim 26, wherein the hydrophilic polymer is formed from a polymerizable monomer selected from the group consisting of acrylates, methacrylates, ethacrylates, acrylic acid, acrylamides, methacrylamides, ethacrylamides and mixtures thereof.

* * * * *